(12) United States Patent
Volgushev

(10) Patent No.: US 10,987,378 B2
(45) Date of Patent: Apr. 27, 2021

(54) UNIVERSAL CARDIOPLEGIC SOLUTION (VARIANTS)

(71) Applicant: LIMITED LIABILITY COMPANY "CARDIOSYSTEMPHARMA" (LLC "CSP"), Khimki Moskovskaya obl. (RU)

(72) Inventor: Valentin Evgenevich Volgushev, Moscow (RU)

(73) Assignee: LIMITED LIABILITY COMPANY "CARDIOSYSTEMPHARMA" (LLC "CSP"), Moskovskaya obl. (RU)

( * ) Notice: Subject to any disclaimer, the term of this patent is extended or adjusted under 35 U.S.C. 154(b) by 0 days.

(21) Appl. No.: 16/843,376

(22) Filed: Apr. 8, 2020

(65) Prior Publication Data

US 2020/0230171 A1 Jul. 23, 2020

Related U.S. Application Data

(62) Division of application No. 15/325,501, filed as application No. PCT/RU2015/000353 on Jun. 5, 2015, now Pat. No. 10,646,511.

(30) Foreign Application Priority Data

Jul. 11, 2014 (RU) .......................... RU2014128455

(51) Int. Cl.
| | | |
|---|---|---|
| A61K 33/06 | (2006.01) |
| A61K 9/08 | (2006.01) |
| A61K 47/02 | (2006.01) |
| A61K 31/047 | (2006.01) |
| A61K 33/00 | (2006.01) |
| A61K 31/133 | (2006.01) |
| A61K 33/14 | (2006.01) |

(52) U.S. Cl.
CPC ................ *A61K 33/06* (2013.01); *A61K 9/08* (2013.01); *A61K 31/047* (2013.01); *A61K 31/133* (2013.01); *A61K 33/00* (2013.01); *A61K 33/14* (2013.01); *A61K 47/02* (2013.01)

(58) Field of Classification Search
CPC .... A61K 31/047; A61K 31/133; A61K 33/00; A61K 33/06; A61K 33/14; A61K 47/02; A61K 9/08; A61P 41/00; A61P 9/00; A61P 9/10
See application file for complete search history.

(56) References Cited

U.S. PATENT DOCUMENTS

| | | |
|---|---|---|
| 5,306,711 A | 4/1994 | Andrews |
| 5,574,019 A | 11/1996 | Segall |
| 5,656,420 A | 8/1997 | Chien |
| 2011/0020475 A1 | 1/2011 | Gygax et al. |
| 2017/0143760 A1 | 5/2017 | Volgushev |

FOREIGN PATENT DOCUMENTS

| | | | |
|---|---|---|---|
| BG | 52177 B2 | 6/1988 | |
| EP | 3 167 874 B1 | 12/2018 | |
| JP | H 9-500380 A | 1/1997 | |
| JP | 2003-520859 A | 7/2003 | |
| RU | 2 145 843 C1 | 2/2000 | |
| RU | 2145843 * | 2/2000 | ............... A01N 1/02 |
| RU | 2 161 405 C2 | 1/2001 | |
| RU | 2 195 878 C2 | 1/2003 | |
| RU | 2 226 093 C1 | 3/2004 | |
| RU | 2226093 * | 3/2004 | |
| WO | WO 95/02326 A1 | 1/1995 | |
| WO | WO 01/54495 A1 | 8/2001 | |

OTHER PUBLICATIONS

Collins et al., "Kidney preservation for transportation. Initial perfusion and 30 hours' ice storage", This Week's Citation Classic, CC/No. 32 (Aug. 11, 1980), p. 288.

Nardi et al., "Warm blood cardioplegia versus cold crystalloid cardioplegia for myocardial protection during coronary artery bypass grafting surgery", Cell Death Discovery, vol. 4, No. 23 (2018), 6 pgs.

Lichtenstein et al., "Intermittent Warm Blood Cardioplegia", Circulation, vol. 92 (Nov. 1, 1995), pp. 341-346.

Franke et al., "Intermittent antegrade warm myocardial protection compared to intermittent cold blood cardioplegia in elective coronary surgery—do we have to change?", European Journal of Cardiothoracic Surgery, vol. 23 (2003), pp. 341-346.

Mora et al., "The Effect of Temperature Management during Cardiopulmonary Bypass on Neurologic and Neuropsychologic Outcomes in Patients Undergoing Coronary Revascularization", The Journal of Thoracic and Cardiovascular Surgery, vol. 112, No. 2 (1996), pp. 514-522.

Martin et al., "Blood Cardioplegia", University Hospital Freiburg, Department of Cardiovascular Surgery, MMCTS (Oct. 9, 2006).

Bokeriya et al., Using a Normothermic Cardioplegic Solution in Myocardial Revascularization (in Russian), Grudnaya i Serdechno-Sosudistaya Khirurgiya, Thoracic and Cardiovascular Surgery, vol. 3 (2006), 6 pgs.

(Continued)

*Primary Examiner* — Anna R Falkowitz
(74) *Attorney, Agent, or Firm* — Paul D. Strain, Esq.; Strain & Strain PLLC

(57) ABSTRACT

This invention relates to medicine, more specifically, to cardiac surgery, and may be used for protecting the heart from ischemia when administering cardioplegia in normothermia or hypothermia. The general-purpose cardioplegic solution contains pharmaceutically acceptable potassium ions; magnesium ions; a base and an acid providing a pH buffer in a range of 7.1-8.9; a diuretic providing osmolality in a range of 275-460 mOsmol/kg. Said solution is used for cardiac protection in cardiopulmonary bypass, as well as for achieving asystole and maintaining the achieved asystole. The procedure for administering the general-purpose cardioplegic solution involves maintaining the achieved asystole by decreasing the flow rate of starting components of said solution relative to the flow rate of autoblood thus decreasing the solution to autoblood ratio.

4 Claims, 2 Drawing Sheets

(56) References Cited

OTHER PUBLICATIONS

Figure 1:
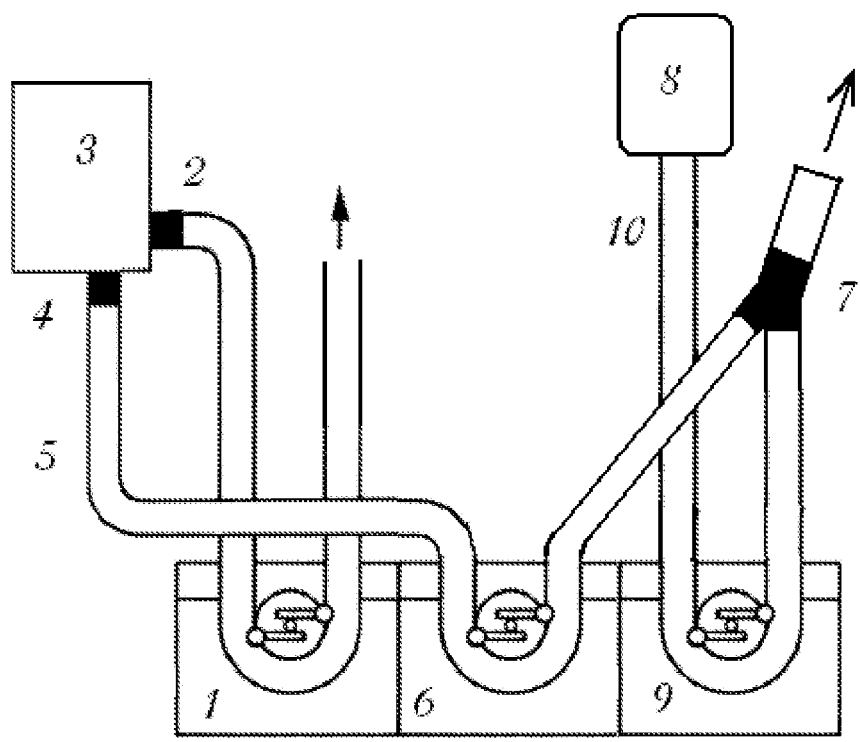

Bokeriya et al., "Normothermic Cardiac Surgery. Comparative Analysis of Hemodynamics in Myocardial Revascularization Operations under Hypo- and Normothermia (in Russian)", Klinicheskaya Fiziologiya Krovoobrashcheniya (Clinical Physiology of Circulation), vol. 3 (2006), 10 pgs.
Romanovsky's Paper, "The Pathophysiological Evaluation of Methods for Myocardium Protection in Coronary Artery Bypass Surgery with Cardiopulmonary Bypass", Extended abstract of Cand. Sci. (Med.), St. Petersburg (2004), 37 pgs.
Morgan et al., "*Clinical Anesthesiology*", Book 2 (transl. from English), M.-SPb: BRShOM-Nevsky Dialect Publ. (2000), 351 pgs.
International Search Report, PCT/RU2015/000353, dated Oct. 8, 2015, 1 pg.
Antiono M. Calafiore et al., "Intermittent Antegrade Warm Blood Cardioplegia", The Society of Thoracic Surgeons (1995), vol. 59, pp. 398-402.
Otani et al, "Protection against Oxygen-Induced Reperfusion Injury of the Isolated Canine Heart by Superoxide Dismutase and Catalase", Journal of Surgical Research, vol. 41, No. 2 (1986). pp. 126-133.
Salerno et al, "Retrograde Continuous Warm Blood Cardioplegia: A New Concept in Myocardial Protection", The Annals of Thoracic Surgery, vol. 51, No. 2 (1991), pp. 245-247.
Ghazy et al., "Is repeated administration of blood-cardioplegia really necessary?", Interactive CardioVascular and Thoracic Surgery, vol. 8, No. 5 (2009), pp. 517-523.
Jacquet et al., "Randomized Trial of Intermittent Antegrade Warm Blood Versus Cold Crystalloid Cardioplegia", The Annals of Thoracic Surgery, vol. 67, No. 2 (1999), pp. 471-477.
Volgushev, U.S. PTO Office Action, U.S. Appl. No. 15/325,501, dated Mar. 7, 2018, 3 pgs.
Volgushev, U.S. PTO Office Action, U.S. Appl. No. 15/325,501, dated Apr. 5, 2019, 4 pgs.
Volgushev, U.S. PTO Office Action, U.S. Appl. No. 15/325,501, dated Oct. 23, 2017, 23 pgs.
Volgushev, U.S. PTO Office Action, U.S. Appl. No. 15/325,501, dated Nov. 28, 2018, 17 pgs.
Volgushev, U.S. PTO Office Action, U.S. Appl. No. 15/325,501, dated May 11, 2018, 37 pgs.
Volgushev, U.S. PTO Office Action, U.S. Appl. No. 15/325,501, dated Jun. 14, 2017, 16 pgs.
Volgushev, U.S. PTO Office Action, U.S. Appl. No. 15/325,501, dated Oct. 8, 2019, 17 pgs.
Volgushev, U.S. PTO Notice of Allowance, U.S. Appl. No. 15/325,501, dated Jan. 16, 2020, 9 pgs.

\* cited by examiner

UNIVERSAL CARDIOPLEGIC SOLUTION (VARIANTS)

CROSS-REFERENCE TO RELATED PATENT APPLICATIONS

This application is a Divisional of U.S. application Ser. No. 15/325,501, filed on Jan. 11, 2017, which is a National Stage of International Application No. PCT/RU2015/000353, filed Jun. 5, 2015, which is based upon and claims the benefit of priority from prior Russian Patent Application No. 2014128455, filed Jul. 11, 2014, the entire contents of all of which are incorporated herein by reference in their entirety.

TECHNICAL FIELD

This invention relates to medicine, more specifically, to cardiac surgery, and may be used for protecting the heart from ischemia when administering cardioplegia.

BACKGROUND OF THE INVENTION

Available cardioplegic solutions and methods for administering cardioplegia are discussed in D. Yu. Romanovsky's paper "The Pathophysiological Evaluation of Methods for Myocardium Protection in Coronary Artery Bypass Surgery with Cardiopulmonary Bypass.". Extended abstract of Cand. Sci. (Med.), St. Petersburg, 2004 [1]. The author identifies the following basic techniques of cardioplegia:

1. Cold crystalloid cardioplegia (CCC) and hypothermic perfusions. In conducting comparative studies, the author used cold crystalloid cardioplegia (CCC) suggested by B. A. Konstantinov in 1981 and based on a consecutive application of two solution formulations: a high-potassium one for cardiac arrest and a low-potassium one for subsequent perfusions. Among the drawbacks of this method are a need to cool the heart and the whole body and the use of a cardioplegic solution as a blood substitute in the myocardium thus creating a substantial risk of surgical complications.

2. Intermittent warm-blood potassium cardioplegia (IWBPC) and normothermic perfusions. The author carried out his comparative studies based on a cardioplegia delivery procedure earlier described by A. M. Calafiore and coauthors (Calafiore A M, Teodori G, Mezzetti A, Bosco G, Verna A M, Di Giammarco G, et al. Intermittent Antegrade Warm Blood Cardioplegia. *Ann Thorac Surg* 1995 February; 59:398-402) involving delivery of a 30% pure potassium chloride solution in the blood cardioplegia line. Thus, said method does not require a special cardioplegic solution. The cardioplegic mixture is a combination of blood and potassium chloride. The disadvantage of this method is a high risk of drug dosage and administration time errors. High potassium levels may result in a failure to restore the heart function, while low potassium levels can lead to a sudden resumption of heart beat, exhaustion of energy resources, and, as a consequence, to myocardial ischemia. A further drawback of this method is that the cardioplegic mixture lacks additional agents to protect the myocardium. This may have negative consequences, when during surgery it becomes necessary to interrupt the delivery of cardioplegia for a long time in order to clean the surgical site from blood.

3. Cold blood potassium cardioplegia (CBPC) and normothermic perfusions ("warm body, cold heart"). This method involves using crystalloid cardioplegic solutions mixed with cold blood for infusion in the heart. To conduct comparative studies, the author "proposed and introduced into clinical practice a simple and generally available solution for delivering blood cardioplegia. Said solution is prepared predominantly based on official solutions using minimum components . . . " Among the drawbacks of this method one should mention its inability to avoid a negative impact of hypothermia on the myocardium, because cold blood stops adequately sustain acid-base and osmotic homeostasis and is unable to penetrate into smallest capillaries due to higher viscosity and interstitial edema.

Further to the above, the following should be noted.

The CCC procedure described in [1], which involves two self-prepared solutions of rather complicated formulations—a high-potassium one for cardiac arrest and a low-potassium one for subsequent perfusions—is rarely used in practice. The reasons are a high labor input required for preparing said solutions and a need to control the quality of resulting drugs. In the majority of cases, cardiac arrest and maintenance of asystole during the CCC procedure are achieved using industrially available crystalloid cardioplegic solutions, for example, Custodiol. For years of application of this procedure, dozens of other formulations for cold cardioplegia have been developed, but the challenge of reducing surgical complications associated with the cooling of the myocardium and the whole body and the use of blood substitute remains pending.

An alternative to cold crystalloid cardioplegia is warm blood cardioplegia, which employs a patient's own warm blood for myocardial protection. However, there are no generally established or commonly obvious technical solutions in this field. Some authors choose to combine cold- and warm-blood cardioplegic procedures. Thus, the use of the IWBPC procedure (potassium chloride injections) [1] carried out without cooling must prevent related complications. However, in the invention RU 2195878 C2 titled Method for Patient Protection in Coronary Artery Bypass Graft Surgery (Oblast Clinical Hospital No 1, Sverdlovsk Oblast) [2], it is suggested to provide an additional protection of the myocardium through cooling it while maintaining a patient's normal body temperature: "The cardioplegic solution is cooled to 6-8° C. and infused into the coronary bed intermittently at 25- to 30-min intervals, while providing additional local cooling of the myocardium by placing sterile crushed ice into the pericardial cavity." The CBPC procedure described in [1] is based on the application of a crystalloid solution for cold blood cardioplegia, i.e., on mixing cold blood and a blood substitute solution. In hypothermia, blood loses its transport function, as its viscosity and hemoglobin oxygen affinity increase, and that, in the best case, makes its use for cardiac protection impractical or, in the worst case, may cause thrombosis of small capillaries, development of myocardial infarction or a stroke affected by microvasculature paralysis as a result of lactic acidosis and hypoosmotic interstitial cerebral edema with multiple organ failure.

In the paper "Blood Cardioplegia" by Juergen Martin and Christoph Benk, University Hospital Freiburg, Department of Cardiovascular Surgery, MMCTS (Oct. 9, 2006). doi: 10.1510/mmcts. 2004.000745 [3], the authors describe various procedures for delivering blood cardioplegia and provide a standard scheme thereof comprising cold induction until complete cardioplegic arrest is achieved, reinfusions of cold blood cardioplegia for 1 min repeated at 20-min intervals, and warm terminal reperfusion prior to releasing the aortic clamp, i.e., when the main phase of the operation is completed. In the paper, mention is made of "continuous warm blood cardioplegia" aimed at preventing any reperfusive myocardial injury prior to the release of the aortic clamp. "However, most surgeons discontinue cardioplegic flow for a few minutes during construction of the distal anastomoses leading to 'unintentional' myocardial ischemia. In addition, cardioplegic overdose is a potential problem using this technique." This explicitly specifies that when applying continuous warm blood cardioplegia prior to the release of the aortic clamp, the authors have no obvious solutions for protecting the myocardium from ischemia, reperfusive damage, and hyperkalemia—the major problems of this method. A similar problem is pointed out in the book by G. E. Morgan and M. S. Mikhail, *Clinical Anesthesiology, Book* 2 (transl. from English), M.-SPb: BRShOM-Nevsky Dialect Publ., 2000 [4], where they mention about the occasional use of continuous warm blood cardioplegia that may be superior to intermittent hypothermic cardioplegia in respect of myocardial protection, but the unavailability of a bloodless field complicates the surgical procedure and, moreover, normothermic cardiac surgery is performed in the absence of hypothermic protection, especially, with respect to the brain.

Consequently, based on the above-mentioned sources one can conclude that to date the techniques of continuous warm blood cardioplegia have not been adequately elaborated and respective special cardioplegic compositions have not been well enough developed.

The closest analog of this invention is a drug claimed in RF patent 2145843 [5] and meant to be used for continuous blood cardioplegia. Said patent covers two solution types—NCS1 and NCS2 (hereinafter NCS stands for Normothermic Cardioplegic Solution) comprising potassium chloride, magnesium sulfate, tris-(hydroxymethyl)-aminomethane (trometamol), and mannitol. The solutions substantially differ in potassium chloride content: in NCS1 (high potassium solution), the concentration of potassium chloride is 7.0-8.0 g/L; magnesium sulfate, 2.17-2.27 g/L; trometamol, 0.06-0.08 g/L; and mannitol, 28.84-34.09 g/L; while in NCS2 (low potassium solution), the concentration of potassium chloride is 1.91-2.08 g/L; magnesium sulfate, 2.17-2.27 g/L; trometamol, 0.04-0.06 g/L; and mannitol, 44.57-49.83 g/L. According to said patent, NCS1 is used for cardiac arrest and NCS2, to maintain asystole. The procedure described in [5] is as follows: "NCS is continuously mixed with blood from the oxygenator in a ratio of 1:4. After aortic cross clamping, NCS is infused into the heart for 6 minutes. A mixture of NCS1 and blood is infused at a rate of 250-300 mL/min. To maintain asystole, a mixture of NCS2 and blood is infused at a rate of 100-150 mL/min in the same ratio-1:4. Upon completion of the intracardiac phase of the operation, the NCS infusion is stopped."

It is known from papers that the disadvantage of NCS1 is a risk of complications during cardiac arrest, while the disadvantage of NCS2 is a risk of restarting ventricular (in about 2.5% of patients) and atrial (in about 5% of patients) activities during the operation (L. A. Bokeriya, V. E. Volgushev, R. R. Movsesyan, R. Aibazov, I. I. Berishvili, and I. Yu. Sigaev. Using a Normothermic Cardioplegic Solution in Myocardial Revascularization (in Russian), *Grudnaya i Serdechno-Sosudistaya Khirurgiya* (Thoracic and Cardiovascular Surgery), No. 4, 2006, p. 5). In addition, the drawback of both NCS1 and NCS2 is a need to make a break for changing the type of solution, which can lead to resumption of cardiac activity and may have an adverse impact on myocardial protection. It should be noted that a need to switch to the other solution may arise not only in the initial phase of cardioplegia when it comes to maintaining asystole but also during the operation in case of spontaneous resumption of cardiac activity. If the bioelectrical activity of the heart resumes during the operation, it is necessary to reinfuse NCS1 and then NCS2 (L. A. Bokeriya, V. A. Lishchuk, I. Yu. Sigaev, M. V. Zatevakhina, D. Sh. Gazizova, L. V. Sadykina, V. E. Volgushev, R. S. Ovchinnikov, A. V. Bulatov, and S. G. Khachatryan. Normothermic Cardiac Surgery. Comparative Analysis of Hemodynamics in Myocardial Revascularization Operations under Hypo- and Normothermia (in Russian). *Klinicheskaya Fiziologiya Krovoobrashcheniya* (Clinical Physiology of Circulation), 2006, No. 3, p. 63).

The disadvantages of the two solution types are as follows:

Creating a risk of myocardial injury due to a possible erroneous disturbance of the sequence of solutions applied;

Reducing the efficiency of cardioplegia management, which is especially critical in pediatric cardiac operations as well as surgeries on newborn babies and low-weight babies at breast;

Increasing logistic expenses on the acquisition and storage of two types of medicinal products.

Searching for high-potency cardioplegic solutions enabling a better myocardial protection, expansion of surgical indications, and reduction of cardiac operative mortality with cardiopulmonary bypass using blood cardioplegia, and possessing such features as versatility, simplicity of preparation and use, and commercial availability is one of the focal areas in designing novel cardioplegic solutions.

SUMMARY OF THE INVENTION

The inventors undertook efforts to further develop the blood cardioplegia approach described in [5], including those targeted at using one cardioplegic solution for both achieving and maintaining asystole.

The inventors analyzed the compositions of cardioplegic solutions discussed in [1-5] as well as the options of infusion therapy applied in cardiac surgery with cardiopulmonary bypass.

The majority of cardioplegic compositions contain potassium chloride and in many cases, magnesium sulfate. It is precisely potassium and magnesium ions that are responsible for cardiac arrest. At the same time, in infusion therapy they often employ special solutions for adjusting pH levels, increasing osmolarity, regulating the ionic composition of blood, compensating blood loss, and filling the volume of the heart-lung machine. Said solutions may also comprise various potassium and magnesium salts. For correct calculation of the volume of cardioplegic solution to be delivered in a patient's blood, it is desirable to express potassium and magnesium contents in terms of the number of potassium and magnesium ions rather than in terms of the volume of respective salts. This simplifies the calculation of the number of ions in the patient's blood when concomitant infusion therapy takes place.

A high-potassium NCS1 solution was prepared according to [5] with a concentration of potassium chloride equal to 7.45 g/L; magnesium sulfate, 2.2 g/L; trometamol, 0.08 g/L; and mannitol, 30 g/L. After sterilization, the pH level was 7.7. Said solution was used for administering blood cardioplegia in coronary bypass surgery and for solution shelf-life control. In [5] it was claimed that the shelf life at room temperature was up to 12 months.

Said solution was used in 18 operations. In the first 9 operations, to achieve asystole, the solution was first infused in a ratio of 1:4 with blood at a rate of 250-300 mL/min for 6 minutes. Seven patients experienced asystole within 1-2 minutes and two patients, within 3-6 minutes. Whenever the other nine patients failed to experience asystole within 3 minutes, the solution to blood ratio was changed to 1:2. That was done for four patients, and all of them experienced asystole within 1 minute after changing the solution to blood ratio, i.e., within 3-4 minutes after starting infusion. After the onset of asystole in the first 9 patients, the solution was infused at a rate of 100-150 mL/min and in a ratio with blood of 1:8. Two patients experienced resumption of ventricular electromechanical activity and 3 patients, atrial activity. In all these cases, the solution to blood ratio was within one minute changed to 1:2, which always led to the reoccurrence of the asystole. The other 9 patients in asystole were also administered the solution at a rate of 100-150 mL/min, but the solution to blood ratio this time was 1:6. In this case, ventricular activity was noted only in one patient. Here, again, the solution to blood ratio was changed to 1:2 within one minute followed by complete asystole resumption. In said 9 patients, before stopping the cardioplegic flow for cleaning the surgical site before performing distal anostomosis, the solution to blood ratio was changed within 1 minute to 1:2. Said 9 patients did not experience resumption of electromecanical cardiac activity either during or after the performance of distal anastomoses.

It was found that after 3 months in storage, the pH level of the NCS1 solution prepared according to [5] began to decrease below the established limit of 7.7. The maintenance of slightly alkaline pH within defined limits is needed to prevent lactic acidosis in cardiac arrest. Therefore, the required volume of trometamol within 0.06-0.08 g/L is insufficient for enabling the initially established level of pH in long storage. This is a major obstacle to commercial production of this drug. To eliminate said obstacle, the inventors increased the volume of trometamol to 0.06-1.0 g/L with the aim to enhance the pH buffer and thus compensate for increasing solution acidity in long-term storage. However, a higher content of trometamol increases the solution's pH. To maintain the pH level, it was proposed to use any pharmaceutically acceptable acid. Using, to this effect, an inorganic acid, such as sulfuric or hydrochloric, requires a higher precision of dosage thereof. Organic acids, such as citric or acetic, are weaker, which makes the adjustment of dosage easier. However, the absolute volume required for organic acids would then be two to three times as great. A possible way is using two types of acids, when, for example, the required pH level of the solution is reached roughly by means of hydrochloric acid and then the exact value is adjusted by means of acetic acid.

Trometamol applied in this composition is a chemical base and can be replaced by any other pharmaceutically acceptable base. For example, if a patient has renal, hepatic or respiratory failure, it is desirable to substitute trometamol for sodium bicarbonate.

For a patient with an apparent renal failure and indication for coronary artery bypass graft surgery, a cardioplegic solution without trometamol was prepared, in which the concentration of potassium chloride was 7.45 g/L; magnesium sulfate, 2.2 g/L; sodium bicarbonate, 2 g/L; and mannitol, 30 g/L. After sterilization, the pH was 7.7. The cardiac operation was successful, and no deterioration of renal function occurred.

A cardiac operation with cardiopulmonary bypass involves a serious risk of development of myocardial or cerebral edema. That is why cardioplegic solutions are generally made hyperosmolar. In [5], mannitol was used to maintain osmolarity within 407-425 mOsmol/kg. In some cases, however, the use of mannitol can lead to hypersensitivity reactions expressed as anaphylactic shock. In this case, it is reasonable to apply other pharmaceutically acceptable diuretics, for example, the ions of sodium, glucose, dextrose, sorbitol, colloid or a combination of these substances.

To maintain osmolarity at a required level of 425 mOsmol/kg in a patient with hypersensitivity to mannitol and indication for coronary artery bypass graft surgery, a cardioplegic solution was prepared, wherein mannitol was substituted for glucose. The concentration of potassium chloride was 7.45 g/L; magnesium sulfate, 2.2 g/L; trometamol, 0.08 g/L; and glucose, 25 g/L. The cardiac operation was successful, and no allergic reactions were observed.

In cardiac surgery, it is not recommended to administer diuretics, if the initial osmolality of a patient's blood plasma is above 320 mOsmol/kg. Such osmolarity values may be common in patients with chronic renal failure, decompensated diabetes. In these cases, it is not reasonable to include diuretics in the cardioplegic solution. When conducting a cardiac operation on such patients, the osmolarity of blood plasma is controlled by special techniques, for example, hemodialysis, regardless of the use of a cardioplegic solution. In our practice, for a patient on hemodialysis suffering from chronic renal failure and having an increased blood osmolarity, who faced coronary artery bypass graft surgery, a cardioplegic solution containing no diuretics was prepared, wherein the concentration of potassium chloride was 7.45 g/L; magnesium sulfate, 2.2 g/L; and trometamol, 0.08 g/L. The cardiac operation was successful, and no deterioration of the patient's condition occurred.

A patient with a hypersensitivity to magnesium sulfate was referred for coronary artery bypass graft surgery. A cardioplegic solution was prepared without magnesium sulfate but with a higher content of potassium chloride. The concentration of potassium chloride was 10 g/L; trometamol, 0.08 g/L; and mannitol, 30 g/L. The cardiac operation was successful, and no allergic reactions were observed. In another case, the patient suffered a myocardial infarction and was at risk of cerebral edema. He was assigned a therapy including, inter alia, intravenous injections of a 25% magnesium sulfate solution at a rate of 20 mL twice a day. For coronary artery bypass graft surgery, a cardioplegic solution was prepared with a lower content of magnesium sulfate-4 mmol/L. The concentration of potassium chloride was 7.45 g/L; magnesium sulfate, 1 g/L; trometamol, 0.08 g/L; and mannitol, 30 g/L. The cardiac operation was successful with no cerebral or myocardial edema detected.

For further research, a modified solution with a higher content of potassium chloride and trometamol was prepared, to which hydrochloric acid was added. The concentration of potassium chloride was 8.38 g/L; magnesium sulfate, 2.34 g/L; trometamol, 0.5 g/L; mannitol, 35.9 g/L; and hydrochloric acid, 3.2 ml/L. The pH level after sterilization was 7.8. Said solution was employed for administering blood cardioplegia in coronary artery bypass surgery (17 operations) as well as for solution shelf-life control. In said operations, the solution was initially infused in a ratio of 1:4 with blood at a rate of 250-300 mL/min. Fourteen patients experienced asystole within 1-2 minutes and one, in the $4^{th}$ minute. When one patient failed to experience asystole within 4 minutes, the solution to blood ratio was changed to 1:2, and the asystole occurred within 1 minute. After the onset of asystole, the solution was infused at a rate of 100-150 mL/min and in a ratio with blood of 1:8. Only one patient experienced resumption of cardiac electromechanical activity, so the solution to blood ratio was within one minute changed to 1:2, and the asystole reappeared. No atrial activity was observed.

Then, a low potassium chloride solution was prepared wherein the concentration of potassium chloride was 3.0 g/L; magnesium sulfate, 2.1 g/L; trometamol, 0.2 g/L; and mannitol, 30 g/L. Acetic acid with pH=7.2 was chosen as a pharmaceutically acceptable acid. After sterilization, the pH was 7.1. The solution thus prepared was employed for administering blood cardioplegia in coronary artery bypass surgery as well as for solution shelf-life control. Said solution was used in 7 operations. The solution was initially infused in the ratio of 1:1 with blood at a rate of 250-300 mL/min. All the 7 patients experienced asystole within 1-2 minutes. After the onset of asystole, the solution was infused at a rate of 100-150 mL/min and in the ratio with blood of 1:4. Only one patient exhibited atrial activity; the solution to blood ratio was hence changed to 1:2 within 1 minute, and the activity stopped.

Finally, a solution with a very high content of potassium chloride and an increased content of trometamol was prepared. The concentration of potassium chloride was 15 g/L; magnesium sulfate, 2.5 g/L; trometamol, 1 g/L; and mannitol, 40 g/L. Citric acid with pH up to 9.0 was taken as a pharmaceutically acceptable acid. After sterilization, the pH level was 8.9. The solution thus prepared was employed for administering blood cardioplegia in coronary artery bypass surgery as well as for solution shelf-life control. Said solution was used in 10 operations. Throughout the operation, the solution was infused at a rate of 100-150 mL/min. To achieve asystole, the solution to blood ratio was made 1:4. All the 10 patients experienced asystole within 1-2 minutes. After the onset of asystole, the solution to blood ratio was made 1:10. No resumption of ventricular or atrial activity was noted.

The technique of varying potassium chloride content in the cardioplegic solution during surgery was tested on 5 patients. To this end, we prepared a cardioplegic solution with a low potassium chloride content. The concentration of potassium chloride was 3.0 g/L; magnesium sulfate, 2.1 g/L; trometamol, 0.2 g/L; mannitol, 30 g/L; and acetic acid, 5.2 mL/L. In addition, a programmable syringe dispenser filled with a 30% potassium chloride solution was employed. The potassium chloride solution was infused from the syringe dispenser into the cardioplegic line, wherein it was mixed with the prepared solution prior to infusing into the coronary bed. In the syringe dispenser, two infusion modes were provided—one for achieving and one for maintaining asystole. The estimated concentrations of potassium chloride in the cardioplegic line were 8.38 g/L and 3.0 g/L, respectively. The cardioplegic mixture was fed at a constant rate of 250 mL/min with a solution to blood ratio of 1:4. To monitor the parameters of the mixture of general-purpose cardioplegic solution and blood at the entry into the B coronary bed as well as blood parameters in the cardiopulmonary bypass system, we used the CDI™ 500 blood parameter monitors (Terumo Cardiovascular Systems Corporation) allowing one to monitor potassium ion content in real time. In the first mode (asystole achievement), all the 5 patients experienced asystole within 1-3 minutes. After the onset of asystole, the syringe dispenser was switched to the asystole maintenance mode. During the cleaning of the surgical site, the cardioplegic flow and the infusion pumps were stopped, but there was no sign of resuming the atrial or ventricular activities.

Tests on the long-term storage of our solutions having a high content of trometamol (up to 1 mg/L) and comprising a pharmaceutically acceptable acid showed that the shelf life of said solutions at room temperature would be at least two years with maintaining the desired pH level in the range of 7.1-8.9. This allows one to commercialize said solutions, which is of significant importance. With pharmacy production of said drugs, immediately before using them, one can add a minimum amount of pharmaceutically acceptable acid, for example, 0.1 mL and trometamol, for example, 0.06 g/L to obtain the desired pH with the solution to blood ratio taken into account.

Eventually, a very broad range of variation in allowable component ratios for the cardioplegic solution has been obtained. Within that range, said solution variants have their individual characteristics making them preferable under certain conditions. Thus, a cardioplegic infusion rate within 250-300 mL/min provides a sufficient blood flow to the heart and a good protection against ischemia even in myocardial hypertrophy. For said rate, a preferable solution would be one containing potassium chloride in the range from 3 to 9 g/L. However, such flow rate may be unacceptable in some pathologies or in pediatric cardiac surgery, because it can lead to myocardial injury. A high infusion rate may also cause hemodilution, which may be undesirable under certain conditions. For low infusion rates (from 20 to 150 mL/min), a preferable solution would be one with a high content of potassium chloride (from 9 to 15 g/L). The proportion of solution components is significantly affected by the solution to blood ratio. Typically, said ratio is 1:4, because it provides enough blood for myocardial protection and, at the same time, ensures a sufficient volume of cardioplegic solution. Said ratio allows one to conduct a long-term cardioplegia and provide an adequate myocardial protection. It is possible, however, to safely reduce this ratio in the range from 1:4 to 1:1 for a short time, in order to accelerate asystole or to saturate the myocardium with solution components prior to interrupting the cardioplegic flow for cleaning the surgical site. We also recommend a temporary reduction of said ratio to 1:1 in case of spontaneous resumption of cardiac function or the emergence of atrial activity until complete asystole resumption is achieved. Increasing the solution to blood ratio from 1:4 to 1:10 is necessary when the same solution is used for maintaining the asystole. In some pathologies of cardiac vessels or in pediatric cardiac surgery, it is preferable to have a continuous low rate of delivering the mixture of blood and cardioplegic solution. In this case, an efficient approach will be using a low-potassium general-purpose solution and a syringe dispenser with a potassium chloride solution for changing the concentration of potassium chloride in the mixture of blood and cardioplegic solution being delivered.

The herein described method of using a cardioplegic solution can be especially effective in normothermic conditions, when the solution itself and the patient's heart and body are not cooled. Using the general-purpose cardioplegic solution provides a possibility to carry out cardioplegia for an unlimited period of time due to the absence of ischemia and reperfusion injuries during and after the infusion thereof. This feature allows one to reduce surgical complications and expands the range of indications for surgery with cardiopulmonary bypass covering those patients for whom cardiac surgery in hypothermia is contraindicated.

Said cardioplegic solution can also be applied under hypothermic conditions in those cases, when hypothermia is a traditional or obligatory practice in a given cardiology clinic, or when emergent situations occur in the course of surgery and it becomes necessary to interrupt the cardioplegic flow for a long time. In these instances, it is recommended to employ surface (31-35° C.) or moderate (25-30°

C.) hypothermia, because a deeper cooling of the cardioplegic solution can impair the protective properties of blood.

The technical result of the invention is to improve myocardial protection, expand the range of indications for surgery, and reduce mortality in cardiac surgery with cardiopulmonary bypass using blood cardioplegia. A further technical result is the generality of the cardioplegic solution.

The novel cardioplegic solution proposed by the inventors herein is called general-purpose, as it allows one
- To use one drug both for achieving asystole and maintaining the achieved asystole, which makes its application convenient, facilitates surgery, mitigates the risk of errors in using solutions, and reduces surgery costs;
- To make said drug commercially available, in which case the shelf life thereof is at least two years while maintaining the required pH level, to prepare the drug immediately before the operation, and to prepare the drug directly in the course of surgery varying its parameters;
- To administer cardioplegia according to a typical or patient-specific scheme;
- To apply directly during surgery various techniques for changing cardioplegic mixture parameters, such as the cardioplegic solution to blood ratio or the concentration of potassium chloride in the cardioplegic solution;
- To use said cardioplegic solution for surgery in both normothermia and hypothermia. Furthermore, the proposed general-purpose cardioplegic solution allows one
- To provide a continuous flow of cardioplegic solution while switching from the cardiac arrest mode to the asystole maintenance mode thus ensuring a continuous myocardial protection;
- To reduce the time interval from the beginning of infusion of the cardioplegic mixture to the occurrence of asystole;
- To mitigate risks associated with a long-term cardiac arrest in asystole, occurrence of cardiac activity and fibrillation prior to the occurrence of asystole, and resumption of cardiac beat while maintaining the asystole;
- To vary the parameters of the cardioplegic mixture directly during surgery depending on the patient's myocardial activity and biochemical blood parameters, whether computer-aided or not.

The subject of the present invention relates to a novel general-purpose cardioplegic solution containing the following pharmaceutically acceptable components:
Potassium ions: 40.2-200.1 mmol/l;
Magnesium ions: 0-24.3 mmol/l;
Base and acid to get the solution's pH of 7.1-8.9;
Distilled water: up to 1000 ml.

The base used in said drug can be any pharmaceutically acceptable base, for example, trometamol or sodium bicarbonate;

The acid used in said drug is one or more pharmaceutically acceptable acids selected from the group of organic or inorganic acids, for example, sulfuric acid, hydrochloric acid, citric acid, acetic acid.

The subject of the present invention relates to a novel general-purpose cardioplegic solution comprising the following pharmaceutically acceptable components:
Potassium ions: 40.2-200.1 mmol/l;
Magnesium ions: 0-24.3 mmol/l;
Base and acid to attain the solution's pH within 7.1-8.9;
A pharmaceutically acceptable diuretic to ensure osmolality within 275-460 mOsmol/kg;
Distilled water: up to 1000 ml.

The diuretic used in said drug can be selected from pharmaceutically acceptable diuretics, for example, mannitol, glucose, dextrose, sorbite.

The preferred composition of the general-purpose cardioplegic solution contains the following components:
Potassium chloride: 7.45 g;
Magnesium sulfate: 2.34 g;
Trometamol: 0.5 g;
Hydrochloric acid: 1M to attain pH 7.6-8.0;
Mannitol: 35.9 g;
Distilled water: up to 1000 ml.

Also, the preferred composition of the general-purpose cardioplegic solution contains the following components:
Potassium chloride: 8.38 g;
Magnesium sulfate: 2.34 g;
Trometamol: 0.5 g;
Hydrochloric acid: 1M to attain pH 7.6-8.0;
Mannitol: 35.9 g;
Distilled water: up to 1000 ml.

The two most preferable compositions (for industrial production of a general-purpose cardioplegic solution) are
A. Containing the Following Components:
Potassium chloride: 7.45 g;
Magnesium sulfate: 2.34 g;
Trometamol: 0.5 g;
Hydrochloric acid: 1M to attain pH 7.6-8.0;
Mannitol: 35.9 g;
Distilled water: up to 1000 ml;
B. Containing the Following Components:
Potassium chloride: 8.38 g;
Magnesium sulfate: 2.34 g;
Trometamol: 0.5 g;
Hydrochloric acid 1M to attain pH 7.6-8.0
Mannitol: 35.9 g;
Distilled water: up to 1000 ml.

Solution B, as distinct from Solution A, has a higher concentration of potassium chloride, which means that with equal delivery volumes, the cardioplegic mixture in this case provides a faster onset of asystole but demands a more rigid control of the volume of solution infused in order to avoid hyperkalemia. Using Solution A reduces the risk of hyperkalemia but increases the risk of a longer cardiac arrest and fibrillation development.

It has been found that in administering blood cardioplegia, a higher volume of potassium chloride delivery into blood reduces the time to the onset of asystole and mitigates risks associated with ventricular fibrillation and cardiac activity in cardiac arrest.

It has been found that it is more efficient to maintain the achieved asystole not by replacing one solution with another (a high-potassium one with a low-potassium one), but rather by varying the volume of delivery of a single general-purpose cardioplegic solution or by changing the proportion of the solution's active components and blood. In so doing, it is possible to vary the volume of potassium chloride contained in the cardioplegic solution using the following techniques:
- Changing solution flow rate relative to blood flow rate;
- Changing the concentration of potassium chloride in the solution while holding solution and blood flow rates constant;
- Changing simultaneously solution and blood flow rates;
- Combining the three techniques mentioned above.

The choice of a specific technique for changing the level of potassium in the cardioplegic mixture depends on the phase of cardioplegia, the experience of the surgical team, and the availability of equipment required for perfusion and for mixing solution components.

The following processes are understood as cardioplegia phases:

Initial asystole achievement. As a rule, when using a solution with an average potassium level (7.45-8.38 g/L) and a ratio of cardioplegic solution and blood equal to 1:4, asystole is achieved within 1-3 minutes and occurs with no ventricular fibrillation or atrial activity. However, some patients begin to experience asystole only in more than 4 minutes and it may occur following via fibrillation, thus adversely affecting myocardial safety. In such cases, we recommend, prior to asystole occurrence, to increase the content of potassium chloride in the solution up to 15 g/L or to change the solution to blood ratio from 1:4 to 1:2 or 1:1 until asystole occurs. To ensure asystole achievement in using a solution with a low potassium level (3.0-7.44 g/L), the cardioplegic solution to blood ratio must be changed from 1:1 to 1:4. When using a solution with a high potassium level (8.39-15 g/L), the cardioplegic solution to blood ratio must be accordingly changed from 1:4 to 1:10;

Secondary asystole achievement (in case the heart suddenly resumes electromechanical activity). Here, to achieve a secondary asystole, we recommend to increase the content of potassium chloride in the solution up to 15 g/L or to decrease the solution to blood ratio;

Maintaining the achieved asystole. In this case, we recommend to decrease the content of potassium chloride in the solution down to 3.0 g/L or to change the solution to blood ratio from 1:4 down to 1:10. If cardiac activity suddenly resumes while the patient is in asystole, then upon achieving a secondary asystole, it is necessary to maintain either a higher level of potassium in the solution or a higher solution to blood ratio;

Preparation for temporary interruption of cardioplegic flow for the time of cleaning the surgical site. The delivery of cardioplegic mixture can be interrupted for 10-30 minutes. It is recommended, one minute before the cessation of cardioplegia delivery, to increase either the content of potassium chloride in the solution (to 15 g/L) or the solution to blood ratio;

Preparation for the termination of cardioplegia and the resumption of cardiac function. It is recommended that 10 minutes before the termination of cardioplegia the content of potassium chloride in the solution should be decreased to 3.0 g/L and the solution to blood ratio should be changed to 1:10.

Said solution components in gram-per-liter concentrations allow one to efficiently solve the problems of cardioplegia and provide protective functions including preservation of the pumping function of the heart, elimination of acidosis, maintenance of the pH level, and prevention of myocardial and cerebral edema. It is to be noted that blood also performs some other myocardial protection functions, such as supplying oxygen and nutrients, eliminating oxidative products, and providing protection against bacterial and viral contamination. It is the use of blood that actually removes constraints on the duration of an operation, in which a general-purpose cardioplegic solution is applied.

The proportion of solution components and blood in the cardioplegic mixture can vary from 1:1 to 1:10. Said proportion depends on the concentration of potassium in the stock solution and the objective to be met in a given phase of cardioplegia delivery. As a rule, cardioplegia is started with a solution to blood ratio of 1:4. Subsequently, whenever a need arises in a sooner onset of asystole or in interrupting the delivery of cardioplegic mixture, said ratio can be increased maximum to 1:1. After the onset of asystole or before the termination of cardioplegia, said ratio can be decreased maximum to 1:10.

The invention is illustrated by the following drawings.

FIG. 1. Scheme for application of general-purpose cardioplegic solution using a heart-lung machine (HLM) roller pump.

1—HLM arterial pump; 2—oxygenator connector for arterial perfusion; 3—oxygenator; 4—oxygenator connector for coronary perfusion; 5—tubing line for coronary blood perfusion; 6—pump for coronary blood perfusion; 7—T-joint for stock solution and blood, 8—vial with stock solution; 9—HLM pump for feeding stock solution; 10—tubing line for coronary perfusion of stock solution.

Figure 2:
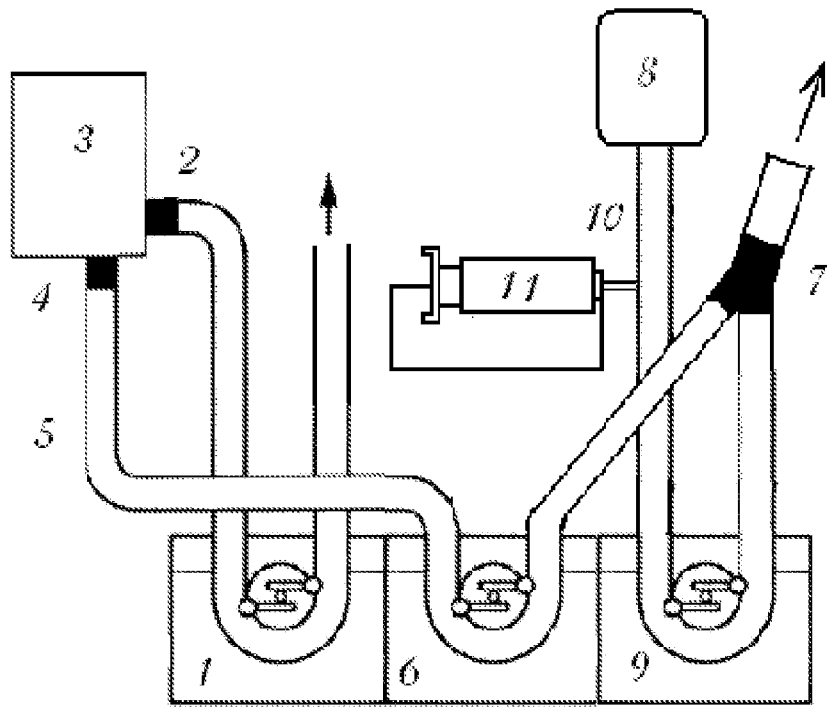

FIG. 2. Scheme for application of general-purpose cardioplegic solution, wherein potassium chloride content is changed during surgery using a syringe dispenser.

1—HLM arterial pump; 2—oxygenator connector for arterial perfusion; 3—oxygenator; 4—oxygenator connector for coronary perfusion; 5—tubing line for coronary blood perfusion; 6—pump for coronary blood perfusion; 7—T-joint for stock solution and blood, 8—vial with stock solution; 9—HLM pump for feeding stock solution; 10—tubing line for coronary perfusion of stock solution; 11—syringe dispenser with potassium chloride solution.

Figure 3:
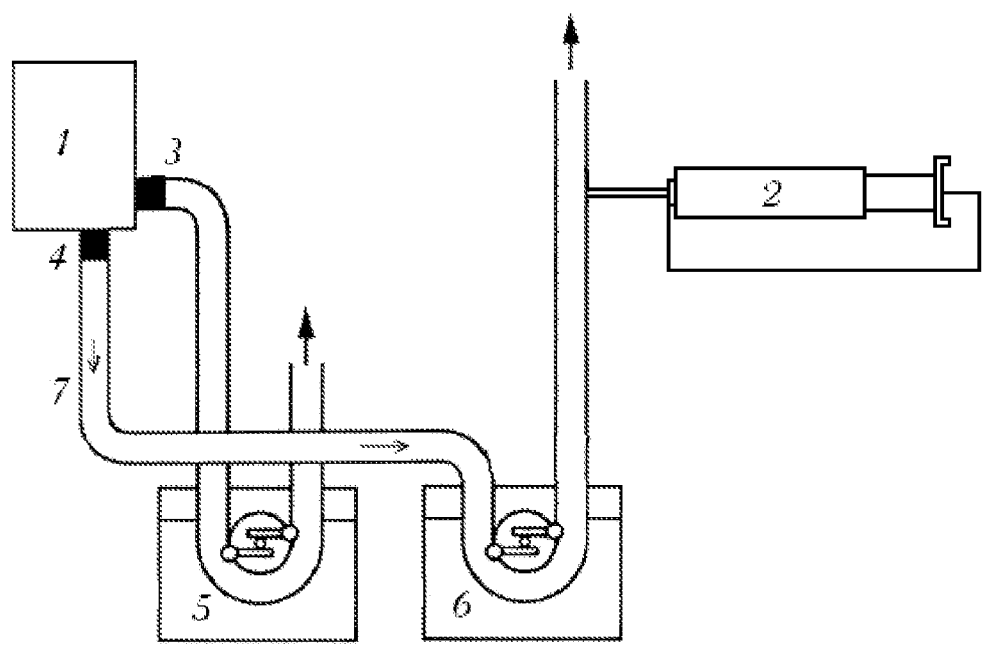

FIG. 3. Scheme for application of general-purpose cardioplegic solution using a syringe dispenser.

1—oxygenator; 2—syringe dispenser with stock solution; 3—oxygenator connector for arterial perfusion; 4—oxygenator connector for coronary perfusion; 5—HLM arterial pump; 6—HLM pump for coronary perfusion; 7—tubing line for coronary blood perfusion.

Examples below illustrate but do not limit this invention.

EXAMPLE 1

Delivery of general-purpose cardioplegic solution (GPCS) using a HLM roller pump (FIG. 1). This is the most universal scheme. Here, GPCS components are as follows:

Potassium chloride: 8.38 g;
Magnesium sulfate: 2.34 g;
Trometamol: 0.5 g;
Mannitol: 35.9 g;
Hydrochloric acid: 1M to attain pH=7.9;
Distilled water: up to 1000 ml.
Osmolality is 440 mOsmol/kg.

After the beginning of surgery and connection of the patient to a heart-lung machine, perfusion is performed at a body and heart temperature maintained within 25-37° C. (the optimum temperature is 36-37° C.). After puncturing the aorta with a cardioplegic cannula, the stock solution is continuously mixed with autoblood from the oxygenator at a ratio of 1:4. To perform cardiac arrest, GPCS is infused into the aortic root or directly into the coronary ostia, while maintaining infusion pressure in the aortic root at max 100 mm Hg. Following aortic cross clamping, GPCS is infused into the heart for 5 minutes to reach a stable cardiac arrest. The rate of GPCS infusion varies from 200 to 350 mL/min. To maintain the asystole, GPCS is infused into the aortic root or directly into the coronary ostia, while maintaining infusion pressure in the aortic root at max 100 mm Hg, or into the coronary sinus, while maintaining GPCS infusion pressure at max 50 mm Hg. To maintain the asystole (the rate of GPCS delivery is slowed down to 50-150 mL/min at a solution to blood ratio of 1:8. GPCS infusion time and volumetric flow rate parameters as well as the ratios of the stock solution and autoblood from the oxygenator are determined by the preoperative concentration of potassium in the patient's blood and the size and mass of his/her heart. Upon passing through the heart, GPCS gets into the general circulation. After the intracardiac phase of surgery is completed, the GPCS delivery is stopped.

EXAMPLE 2

GPCS delivery using a HLM roller pump, wherein potassium chloride content is changed during surgery using a syringe dispenser (FIG. 2). This scheme is more preferable in cardiovascular pathologies, when it is desirable to keep the rate of cardioplegic mixture perfusion at a constant level. Here, GPCS components are as follows:
  Potassium chloride: 3.0 g;
  Magnesium sulfate: 2.1 g;
  Trometamol: 0.2 g;
  Mannitol: 30.0 g;
  Acetic acid: 1M to attain pH=7.1;
  Distilled water: up to 1000 ml.

The syringe dispenser is filled with a 30% potassium chloride solution.

After the beginning of surgery and connection of the patient to a heart-lung machine, perfusion is performed with keeping the temperatures of the body and the heart within 25-37° C. (the optimum temperature is 36-37° C.). After puncturing the aorta with a cardioplegic cannula, the stock solution is continuously mixed with autoblood from the oxygenator at a ratio of 1:5. GPCS is infused into the aortic root or directly into the coronary ostia, while maintaining infusion pressure in the aortic root at max 100 mm Hg. The rate of potassium chloride flow from the syringe dispenser is adjusted such that the concentration in the cardioplegic line is 8.0 g/L. On achieving asystole, along with GPCS infusion, the solution from the syringe dispenser is fed for 5 minutes to reach a stable cardiac arrest. In maintaining the asystole, the delivery of the solution from the syringe dispenser is stopped while that of GPCS continues. The delivery of GPCS can be interrupted for cleaning the surgical site for up to 20 minutes. If the heart activity is suddenly resumed, along with GPCS infusion, potassium chloride solution is fed from the syringe dispenser until a complete cardiac arrest is reached. Upon passing through the heart, GPCS gets into the general circulation. After the intracardiac phase of surgery is completed, the GPCS delivery is stopped.

EXAMPLE 3

GPCS infusion using a syringe dispenser (FIG. 3). This scheme is more preferable in pediatric surgery and hemodynamically significant pathologies of myocardial vasculature or when hemodilution is undesirable. Here, GPCS components are as follows:
  Potassium chloride: 15.0 g;
  Magnesium sulfate: 2.5 g;
  Trometamol: 1.0 g;
  Mannitol: 40.0 g;
  Citric acid: 1M to attain pH=8.9;
  Distilled water: up to 1000 ml.

After the beginning of surgery and connection of the patient to a heart-lung machine, GPCS perfusion is performed with keeping the temperatures of the body and the heart within 25-37° C. (the optimum temperature is 36-37° C.). After puncturing the aorta with a cardioplegic cannula, GPCS fed by an electronic syringe dispenser and oxygenated autoblood fed by an HLM roller pump are mixed in a ratio of 1:4. To perform cardiac arrest, GPCS is infused into the aortic root or directly into the coronary ostia, while infusion pressure in the aortic root is maintained at max 100 mm Hg. The initial infusion of GPCS is made within 3-4 minutes after aortic cross clamping and then for another minute after cardiac arrest to ensure a stable asystole. Depending on the preoperative concentration of potassium in the patient's blood and the size and mass of his/her heart, the volumetric rate of stock solution flow from the syringe dispenser varies from 40 to 70 mL/min and the rate of autoblood flow from the HLM oxygenator varies from 160 to 280 mL/min. Upon achieving a stable asystole, the GPCS volumetric flow rate is decreased. The objective of this phase is to maintain the asystole in a stable state. To this end, the volumetric rate of stock solution delivery from the dosage syringe dispenser is slowed down to 6-17 mL/min, while the volumetric flow rate of oxygenated autoblood fed from the HLM roller pump in a ratio from 1:8 to 1:10 is simultaneously decreased to 48-136 mL/min. GPCS infusion time and volumetric flow rate parameters as well as the ratios of the stock solution and autoblood from the oxygenator are determined by the preoperative concentration of potassium in the patient's blood and the size and mass of his/her heart. To maintain the asystole, GPCS is infused into the aortic root or directly into the coronary ostia, with infusion pressure in the aortic root maintained at max 100 mm Hg, or into the coronary sinus, with GPCS infusion pressure maintained at max 50 mm Hg.

INDUSTRIAL APPLICABILITY

This invention can be applied in human and veterinary medicine.

The invention claimed is:
1. A method of providing blood cardioplegic heart protection at a temperature of 25-37° C. using a cardioplegic solution, the method comprising:
  providing the cardioplegic solution comprising:
    potassium chloride: 3-15 g;
    magnesium sulfate: 0-2.93 g;
    diuretic providing osmolarity within 275-460 mOsmol/kg;
    acid and base to attain the solution's pH within 7.1-8.9;
    distilled water: up to 1000 ml;
  administering via a single injection the cardioplegic solution to a patient in need thereof in a mixture with the patient's autoblood in a ratio from 1:1 to 1:10,
  maintaining the patient, the patient's autoblood, and the mixture at a temperature of 25-37° C. using a heart-lung machine,
  wherein before, during, or after the single injection, no further injections of the cardioplegic solution or another cardioplegic solution are applied.

2. A method of preparing the cardioplegic solution according to claim 1, the method comprising:
  providing up to 1000 ml of distilled water;
  adding to the distilled water between 3 and 15 g of potassium chloride;
  adding to the distilled water between 0 and 2.93 g of magnesium sulfate;
  adding a pharmaceutically acceptable diuretic to maintain osmolarity in a range of 275-460 MOsmol/kg;
  adding an acid and/or a base to maintain pH in a range of 7.1-8.9.

3. A method of providing blood cardioplegic heart protection at a temperature of 25-37° C. using a cardioplegic solution, the method comprising:
- providing the cardioplegic solution having the following composition:
  - potassium chloride: 7.45 g;
  - magnesium sulfate: 2.34 g;
  - mannitol: 35.9 g;
  - trometamol: 0.5 g;
  - hydrochloric acid: 1M to attain pH 7.6-8.0;
  - distilled water: up to 1000 ml; and
- administering via a single injection the cardioplegic solution to a patient in need thereof in a mixture with the patient's autoblood in a ratio from 1:1 to 1:10,
- maintaining the patient, the patient's autoblood, and the mixture at a temperature of 25-37° C. using a heart-lung machine,
- wherein after the single injection, no further injections of the cardioplegic solution or another cardioplegic solution are applied unless the patient's heart ventricles become active.

4. A method of preparing a cardioplegic solution, the method comprising:
- providing up to 1000 ml of distilled water;
- adding to the distilled water 7.45 g of potassium chloride;
- adding to the distilled water 2.34 g of magnesium sulfate;
- adding 35.9 g of mannitol;
- adding 0.5 g of trometamol;
- adding an 1M HCl to maintain pH in a range of 7.6-8.0.

* * * * *